US011278717B2

(12) United States Patent
Steigauf et al.

(10) Patent No.: US 11,278,717 B2
(45) Date of Patent: Mar. 22, 2022

(54) IMPLANTABLE MEDICAL ELECTRICAL LEAD CONSTRUCTION AND ASSOCIATED IMPLANT SYSTEMS

(71) Applicant: Medtronic, Inc., Minneapolis, MN (US)

(72) Inventors: Thomas J. Steigauf, Richfield, MN (US); Eric H. Bonde, Minnetonka, MN (US); Phillip C. Falkner, Minneapolis, MN (US); Jeevan M. Prasannakumar, Circle Pines, MN (US); Brian T. Stolz, Bloomington, MN (US); John Shishilla, Medina, MN (US); Adam J. Rivard, Blaine, MN (US); Robert Sandgren, Lindstrom, MN (US); Seth Humphrys, Golden Valley, MN (US); Bernard Li, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 407 days.

(21) Appl. No.: 16/114,445

(22) Filed: Aug. 28, 2018

(65) Prior Publication Data
US 2019/0060636 A1     Feb. 28, 2019

Related U.S. Application Data

(60) Provisional application No. 62/661,934, filed on Apr. 24, 2018, provisional application No. 62/551,320, filed on Aug. 29, 2017.

(51) Int. Cl.
*A61N 1/05*     (2006.01)
*A61N 1/08*     (2006.01)
*A61N 1/375*     (2006.01)

(52) U.S. Cl.
CPC ......... *A61N 1/0504* (2013.01); *A61N 1/0551* (2013.01); *A61N 1/08* (2013.01); *A61N 1/375* (2013.01); *A61N 1/0514* (2013.01); *H01R 2201/12* (2013.01)

(58) Field of Classification Search
CPC ...... A61N 1/0504; A61N 1/0551; A61N 1/08; A61N 1/375
See application file for complete search history.

(56) References Cited

U.S. PATENT DOCUMENTS

| | | |
|---|---|---|
| 4,374,527 A | 2/1983 | Iversen |
| 6,104,960 A | 8/2000 | Duysens et al. |
| 6,289,250 B1 | 9/2001 | Tsuboi et al. |
| 6,580,949 B1 | 6/2003 | Tsuboi et al. |
| 6,920,361 B2 | 7/2005 | Williams |
| 7,831,311 B2 | 11/2010 | Cross, Jr. et al. |
| 7,925,358 B2 | 4/2011 | Belden et al. |
| 8,204,569 B2 | 6/2012 | Gerber et al. |

(Continued)

OTHER PUBLICATIONS

International Search Report and Written Opinion for PCT/US2018/048233, dated Nov. 21, 2018, 17 pages.

*Primary Examiner* — Joseph M Dietrich
(74) *Attorney, Agent, or Firm* — Mueting Raasch Group

(57) ABSTRACT

A temporary medical electrical lead includes a connector pin and a single conductor coil. The coil being close-wound and having no turns of the coil distal portion being mechanically coupled together. The coil distal portion translates a force of no greater than 0.1 lb$_f$ (0.4 N) when strained 400%.

17 Claims, 11 Drawing Sheets

(56) References Cited

U.S. PATENT DOCUMENTS

| | | |
|---|---|---|
| 8,332,050 B2 | 12/2012 | Perrey et al. |
| 9,427,571 B2 | 8/2016 | Sage et al. |
| 9,545,207 B2 | 1/2017 | Clark et al. |
| 9,700,731 B2 | 7/2017 | Nassif et al. |
| 2005/0090884 A1 | 4/2005 | Honeck |
| 2007/0255370 A1 | 11/2007 | Bonde et al. |
| 2007/0282411 A1 | 12/2007 | Franz et al. |
| 2008/0208133 A1 | 8/2008 | Lieberman et al. |
| 2011/0257500 A1 | 10/2011 | Wells et al. |
| 2012/0271385 A1 | 10/2012 | Li et al. |
| 2014/0031661 A1 | 1/2014 | Clark et al. |
| 2014/0081363 A1 | 3/2014 | Clark et al. |
| 2014/0350653 A1 | 11/2014 | Shiroff et al. |
| 2015/0100106 A1 | 4/2015 | Shishilla et al. |
| 2016/0213943 A1* | 7/2016 | Mauger ................ A61N 2/006 |
| 2016/0235967 A1* | 8/2016 | Shan ................ A61N 1/36071 |
| 2018/0078760 A1 | 3/2018 | Lee et al. |

\* cited by examiner

IMPLANTABLE MEDICAL ELECTRICAL LEAD CONSTRUCTION AND ASSOCIATED IMPLANT SYSTEMS

FIELD

The present disclosure pertains to medical electrical stimulation, and more particularly to constructions of, and systems including implantable medical electrical leads suitable for selective nerve stimulation, for example, stimulation of the sacral nerves.

BACKGROUND

Neurostimulation, via a medical electrical lead that is implanted with at least one stimulation electrode positioned on or near the sacral nerves, can provide control over urinary incontinence or other pelvic floor disorders. Typically, this stimulation is initially evaluated with what is known as a trialing, or temporary lead that is implanted for a relatively short period of time, for example, seven to thirty days, in order to determine if and how a patient will respond to such stimulation. FIG. 1 is a schematic showing such a temporary medical electrical lead 200 percutaneously implanted for stimulation of a patient's sacral nerves, wherein lead 200 extends through an incision 6 at a dorsal surface 5 of the patient's body 3 and through one of a series of holes or foramina 4 of a patient's sacrum 2.

SUMMARY

The present disclosure relates to constructions of, and systems including implantable medical electrical leads suitable for selective nerve stimulation, for example, stimulation of the sacral nerves. The implantable medical electrical leads may be temporary medical electrical leads that form a single conductor coil. The single conductor coil may be strained at least 300% or 400% and may not transmit a force greater than 0.1 $lb_f$ (0.4 N).

In one aspect, a temporary medical electrical lead includes a connector pin and a single conductor coil. The coil extending from a proximal portion to a distal portion and having a length. The coil being close-wound along the length. The proximal portion of the coil is coupled to the connector pin and a distal portion of the coil extends to a distal-most tip of the lead. The distal portion of the coil defines an inner surface of the lead. The inner surface surrounding an elongate lumen of the lead. The connector pin includes an elongate bore that defines a proximal-most portion of the elongate lumen and a proximal opening thereto at a proximal end of the connector pin. No turns of the coil distal portion are mechanically coupled together. The coil distal portion translates a force of no greater than 0.1 $lb_f$ (0.4 N) when strained 400%.

In another aspect, a system for providing temporary medical electrical stimulation includes the temporary medical electrical lead described herein, an introducer needle, a stylet, and a grip tool. The introducer needle has a lumen sized to receive passage of an entire length of the lead therethrough, from a proximal opening of the needle lumen to a distal opening of the needle lumen. The entire length of the lead is defined from the proximal end of the connector pin to the distal-most tip of the lead. The stylet includes a proximal length and a distal length. The distal length has an outer diameter sized to fit in sliding engagement within the elongate lumen of the lead. The proximal length has an outer diameter sized to abut the proximal end of the connector pin of the lead, when the distal length is fitted within the lead lumen. The grip tool is configured to engage with the lead and the stylet to temporarily secure the stylet to the lead when the distal length of the stylet is fitted within the elongate lumen of the lead, and when the proximal length of the stylet abuts the connector pin of the lead.

In another aspect, a method for assembling a system includes, the temporary medical electrical stimulation includes the temporary medical electrical lead described herein, and a stylet. The stylet is configured to fit in sliding engagement within the elongate lumen of the lead. The method includes inserting a distal length of the stylet into the elongate lumen of the lead from the proximal opening thereof, until the distal length of the stylet abuts the distal-most tip of the lead; and securing the lead to the inserted stylet. The securing includes fitting a distal portion of a grip tool around the lead connector pin and a proximal portion of the grip tool around a proximal length of the inserted stylet, so that the proximal end of the connector pin abuts the proximal length of the inserted stylet.

The above summary is not intended to describe each embodiment or every implementation of the present disclosure. A more complete understanding will become apparent and appreciated by referring to the following detailed description and claims taken in conjunction with the accompanying drawings. In other words, these and various other features and advantages will be apparent from a reading of the following detailed description.

DETAILED DESCRIPTION

Figure 1:
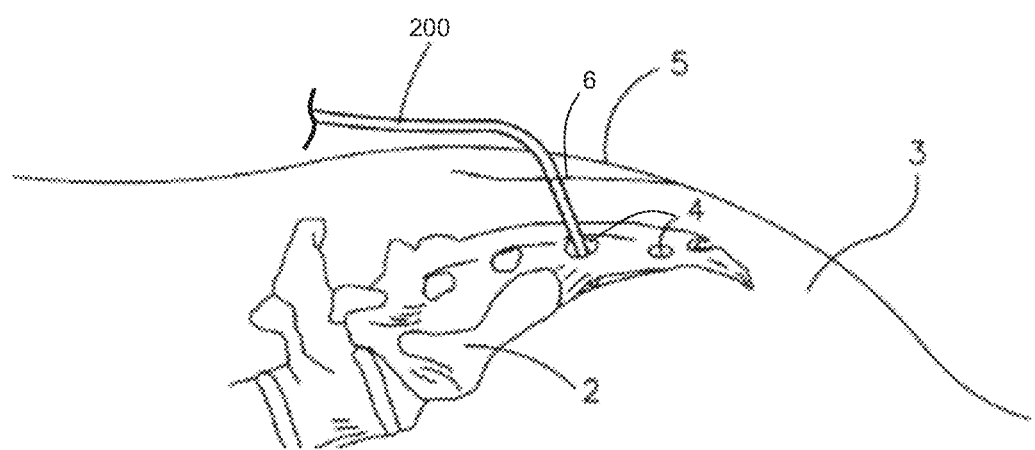
FIG. 1 is a schematic diagram of a temporary medical electrical lead percutaneously implanted for stimulation of a patient's sacral nerves.

The following detailed description is exemplary in nature and is not intended to limit the scope, applicability, or configuration of inventive embodiments disclosed herein in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art. Embodiments will hereinafter be described in conjunction with appended drawings wherein like numerals/letters denote like elements. The drawings are not to scale (unless so stated) and are intended for use in conjunction with the explanations of this detailed description.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The present disclosure relates to constructions of, and systems including implantable medical electrical leads suitable for selective nerve stimulation, for example, stimulation of the sacral nerves. The implantable medical electrical lead may be temporary medical electrical lead that form a single conductor coil. The single conductor coil may be strained at least 300% or 400% and may not transmit a force greater than 0.1 $lb_f$ (0.4 N). The single conductor coil may be strained to elongated to three or four times its original coiled length without transmitting a force greater than 0.1 $lb_f$ (0.4 N) to a distal end of the single conductor coil. Thus, once implanted, the length of the coil can be stained to least 300% or 400% while not overcoming the fixation force of the distal end lead electrode. The distal end lead electrode does not migrate or dislodge from its implantation site even at high strain levels applied to the remaining coil length. While the present disclosure is not so limited, an appreciation of various aspects of the disclosure will be gained through a discussion of the examples provided below.

Figure 5:
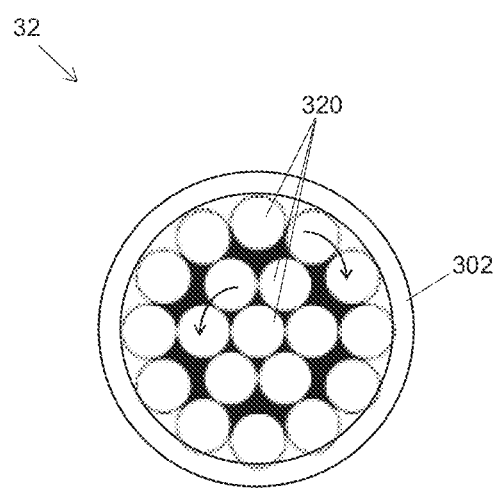
FIG. 5 is a schematic cross-sectional view of the illustrative cable forming the single conductor coil and conductive filaments the cable arranged in a 1×19 configuration.

The conductor coil may be formed of a conductive material that exhibits the spring constant and elastic range described herein. The conductive cable forming the close wound conductor coil may have any useful configuration. FIG. 5 illustrates a 1×19 configuration of the conductive cable where conductive filaments of the cable are arranged in a concentric lay, which is known in the art, where a single filament is surrounded by six filaments forming seven inner filaments and twelve outer filaments surround the seven inner filaments. Another useful configuration is a 1×7 configuration, where conductive filaments of the cable are arranged in a concentric lay, where a single filament is surrounded by six filaments. A further configuration is a 1×3 configuration.

The conductive cable may have a diameter in a range from about 0.004 inch to 0.008 inch (100 micrometers to 200 micrometers), or about 0.006 inch (150 micrometers). The conductive cable is tightly wound into a coil arrangement. The coil diameter may be from about 0.022 inch (560 micrometers) to about 0.045 inch (1140 micrometers), or from 0.034 inch (860 micrometers) to about 0.041 inch (1040 micrometers).

The conductor coil may be formed of a cobalt-nickel alloy such as a material commercially available under the trade designation MP35N. The conductor coil may be formed of an annealed or partially annealed stainless-steel material. The conductor coil may be formed beta-titanium alloy material.

The conductor coil or conductor cable may be formed of a beta-titanium alloy wire. Beta-titanium wire includes titanium with molybdenum, niobium, tantalum, zirconium, chromium, iron and tin. The beta-titanium wire or cable may be heated to a stress-relieve temperature of the beta titanium alloy to allow the wire or cable to retain a desired configuration while remaining ductile. The beta-titanium cable or wire may also be made with low resistance core materials to reduce the wire resistivity. The core materials can be Ta, Nb, Mo, W, Ag, Au. Two or more core materials may be used together.

One useful beta-titanium alloy is Ti-15Mo alloy material. The term "Ti-15Mo" refers to a metastable beta-titanium alloy that includes about 15 weight percent molybdenum. This Ti-15Mo alloy material is commercially available.

Four ETFE coated 1×7 cables (MP35N, annealed stainless steel, partially annealed stainless steel, and Ti-15Mo—each having a 0.006 inch (150 micrometers) diameter were wound into a coil having a diameter from 0.034 inch (860 micrometers) to 0.041 inch (1040 micrometers). Tensile, spring constant and elastic range tests were performed on each coil. The Ti-15Mo coil exhibited the lowest spring constant that was about 2.5 times lower than the MP35N coil. The Ti-15Mo coil had the highest elastic range that was about 4 times higher than the annealed stainless-steel coil.

The Ti-15Mo coil exhibited a spring constant of less than about 0.04 $lb_f$/in (7 N/m) at a coil diameter in a range from about 0.034 to 0.041 inch (860 to 1140 micrometers). At a coil diameter of about 0.034 inch (860 micrometers) the Ti-15Mo coil exhibited a spring constant of about 0.04 $lb_f$/in (7 N/m), and the remaining three coils (at 0.034 inch (860 micrometers) diameter) exhibited a spring constant of at least 0.08 $lb_f$/in (14 N/m). At a coil diameter of about 0.041 inch (1040 micrometers) the Ti-15Mo coil exhibited a spring constant of about 0.02 lb$_f$/in (3.5 N/m), and the remaining three coils (at 0.041 inch (1040 micrometers) diameter) exhibited a spring constant of at least 0.04 lb$_f$/in (7 N/m).

The Ti-15Mo coil exhibited an elastic range of at least about 200% at a coil diameter in a range from about 0.034 to 0.041 inch (860 to 1140 micrometers). At a coil diameter of about 0.034 inch (860 micrometers) the Ti-15Mo coil exhibited an elastic range of at least about 210%, and the remaining three coils (at 0.034 inch diameter (860 micrometers)) exhibited an elastic range of less than about 110%. At a coil diameter of about 0.041 inch (1040 micrometers) the Ti-15Mo coil exhibited an elastic range of at least about 375%, and the remaining three coils (at 1040 micrometers (0.041 inch) diameter) exhibited an elastic range of less than about 150%.

The tensile curve of the four coils showed the Ti-15Mo coil had the lowest spring constant and largest elastic range. A low modulus coil is desired for the temporary medial electrical lead since it can be stretched with less resistance which will reduce lead migration. The Ti-15Mo coil had the lowest modulus of the four coils. Using a Ti-15Mo coil may reduce lead migration and increase lead life as compared to the four tested coils.

Figure 2A:
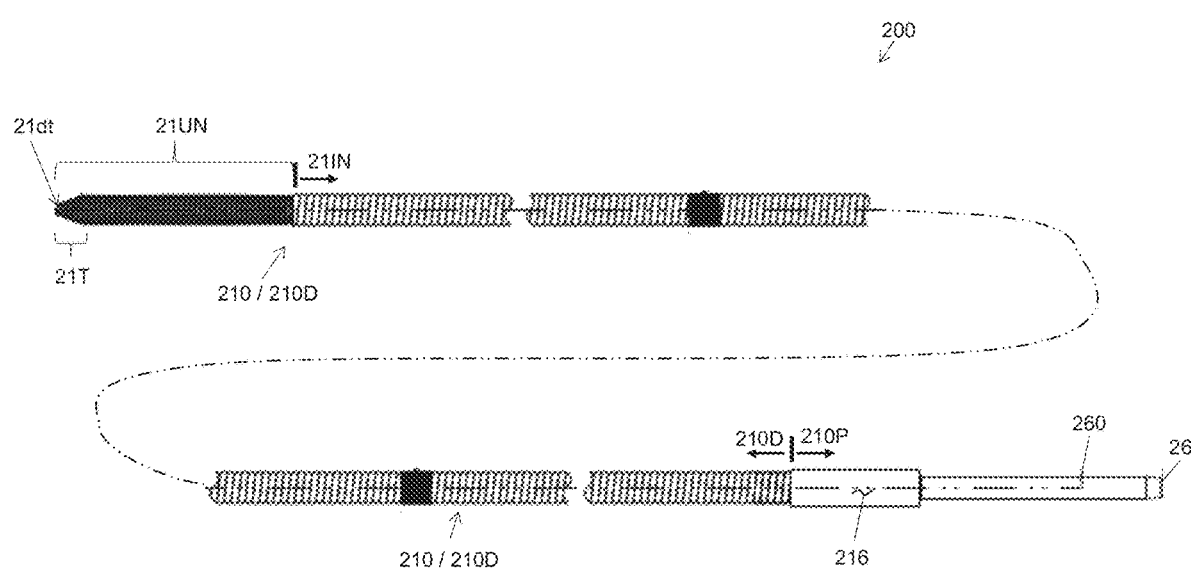
FIG. 2A is a schematic plan view of an illustrative temporary medical electrical lead.

FIG. 2A is a plan view of temporary medical electrical lead 200, according to some embodiments. FIG. 2A illustrates lead 200 including a single conductor coil 210 and a connector pin 260, which together define an entire length of lead 200, from a proximal end 26 of connector pin 260 to a distal-most tip 21$dt$ of lead 200.

Conductor coil 210 is preferably close-wound along an entire length thereof, wherein the entire length of coil 210 is defined by a proximal portion 210P thereof and a distal portion 210D thereof. The close-wound nature of coil 210 can make lead 200 more responsive to push forces applied by an operator, in proximity to connector pin 260, when implanting lead 200, as described in greater detail below. According to the illustrated embodiment, coil proximal portion 210P, which is coupled to connector pin 260, extends within an outer sleeve 216 (for example, a medical grade polymer shrink tubing, such as Polyethylene Teraphthalate or Fluorinated Ethylene Propylene, or a combinations thereof), and coil distal portion 210D extends distally from proximal portion 210P to distal-most tip 21$dt$, being inclusive thereof, with no turns of distal portion 210D being mechanically coupled together. FIG. 2A further illustrates lead distal-most tip 21$dt$ being defined by a tapered segment 21T of coil 210, according to an embodiment described in greater detail below.

Figure 2B:
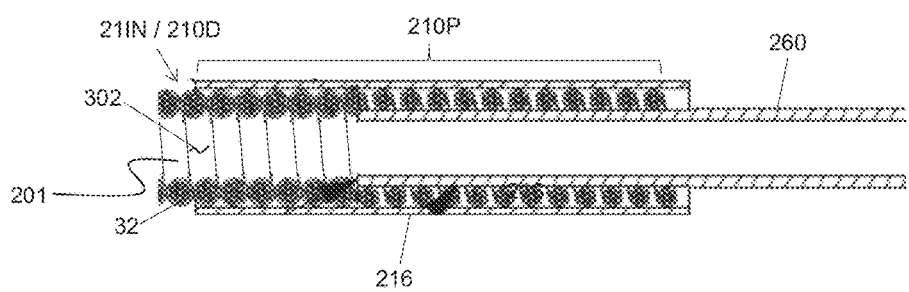
FIG. 2B is a schematic longitudinal section view of the coupling, or junction, between coil proximal portion and connector pin of the illustrative temporary medical electrical lead shown in FIG. 2A.

FIG. 2B is a longitudinal section view of the coupling, or junction, between coil proximal portion 210P and connector pin 260, according to some embodiments. FIG. 2B illustrates coil proximal portion 210P overlapping a distal section of connector pin 260, for example, being soldered or welded thereto, and having the aforementioned sleeve 216 fitted thereabout, for example, via a heat shrink fit.

Figure 2C:
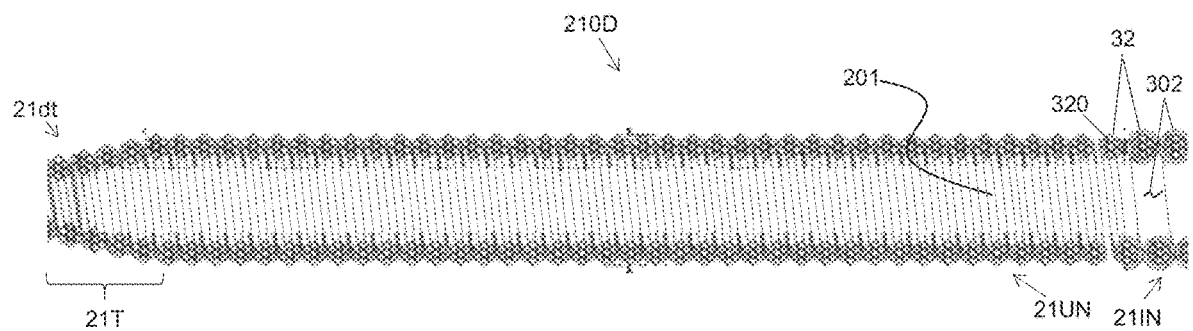
FIG. 2C is a schematic side elevation view of the coil distal portion of the illustrative temporary medical electrical lead shown in FIG. 2A.

With further reference to FIG. 2A, in conjunction with the longitudinal section view of FIG. 2C, coil distal portion 210D includes an insulated proximal segment 211N and an uninsulated distal segment 21UN, wherein uninsulated distal segment 21UN, which may have a length of about 2 to 5% of the total length of the lead 200 about 0.25 inch (6.35 millimeters) in some embodiments having a 12 inch (305 millimeters) lead length, functions as an electrode, for example, to stimulate the aforementioned sacral nerves when lead 200 is implanted as depicted in FIG. 1.

According to embodiments of the present invention, coil distal portion 210D is configured to prevent uninsulated segment/electrode 21UN from migrating or dislodging from the sacral nerve stimulation site over the course of the aforementioned stimulation evaluation, or trialing period, without the need for a fixation component, which may complicate the construction of lead 200. With further reference to FIG. 1, we discovered that the part of lead 200 extending within the sacral region of the body, for example, in proximity to incision 6, can be subject to surprisingly large strains (for example greater than 300%) induced by movement of the patient over the course of the trialing period, for example, as depicted in the schematics of FIG. 3.

Figure 3:
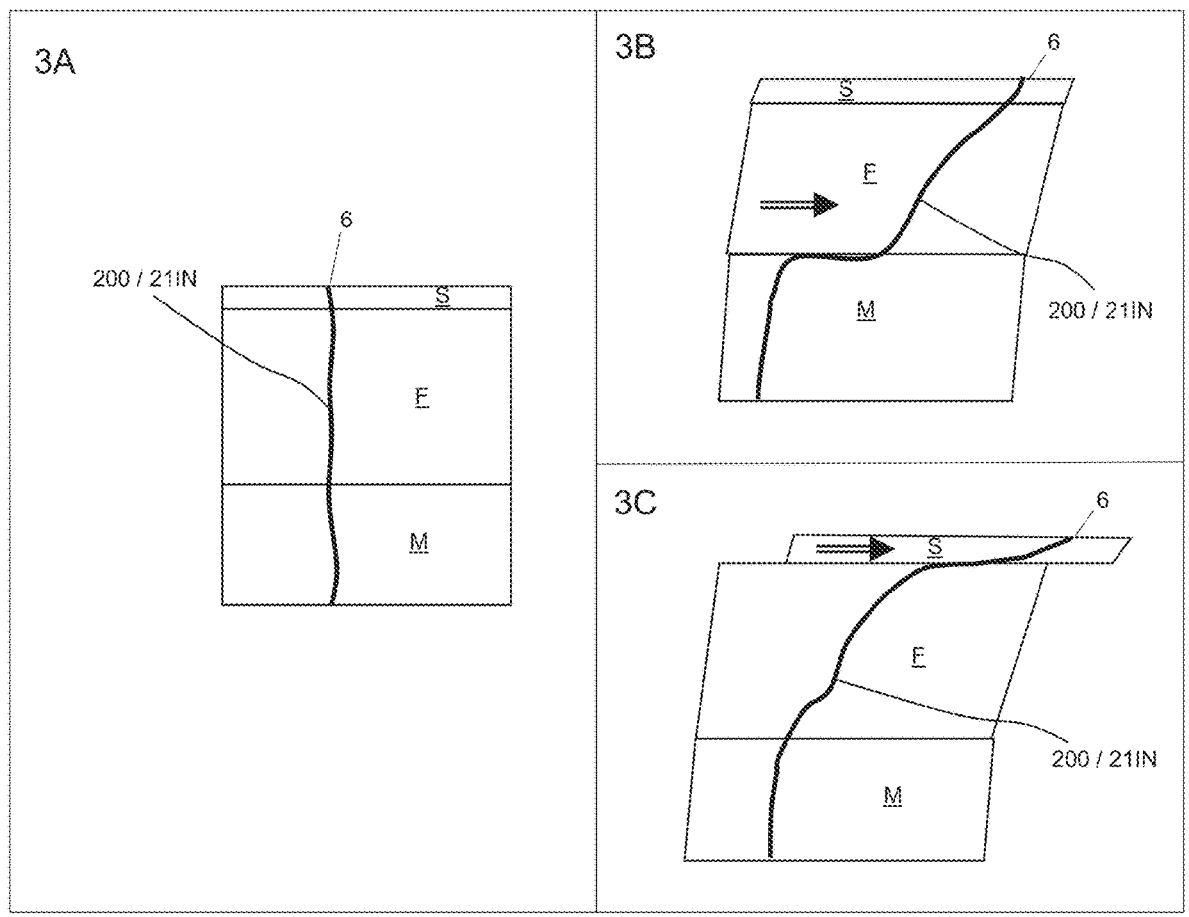
FIG. 3 illustrates three conditions 3A, 3B and 3C where the illustrative temporary medical electrical lead shown in FIG. 2A is stained through strata of skin, fat, and muscle.

In FIG. 3, insulated proximal segment 211N of lead 200 is shown extending through strata of skin S, fat F, and muscle M, in a sacral region, for example, the region adjacent to incision 6. The schematic of FIG. 3A represents an initial position of segment 21N at the time of implant, while the schematics of FIGS. 3B-C represent models (inspired by data collected from computerized tomography (CT) visualization of implanted metallic beads in human cadavers and live sheep, respectively) of potential strains imparted to lead 211N by the movement of skin S, and fat F relative to the underlying muscle M.

In the cadaver studies, we found these strains to be higher than anticipated—for example, greater than 300%, or greater than 350% or greater than 400%. Thus, coil distal portion 210D is preferably configured to absorb 300%, or 350% or 400% strain (in other words, elongate 400%) without transmitting a force that would cause uninsulated distal segment/electrode 21UN to migrate, or dislodge from the sacral nerve stimulation site.

In animal studies, the lowest force recorded that initiated movement of uninsulated segment 21UN was found to be about 0.135 lb$_f$ (0.6 N) so, according to preferred embodiments, coil distal portion 2100 translates a force of no greater than 0.1 lb$_f$ (0.4 N), or, preferably, less than 0.1 lb$_f$ (0.4 N), when subjected to a 300%, or 350%, or 400% strain.

Figure 4:
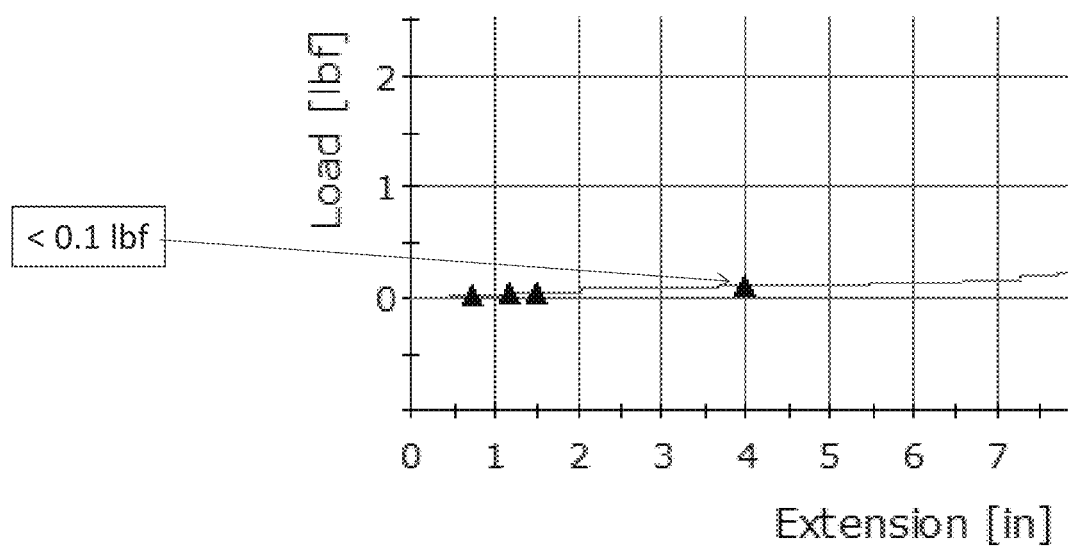
FIG. 4 is a graph of force, or load ($lb_f$) versus extension (inches) for a sample from an exemplary embodiment of lead coil that has a one-inch gauge length.

FIG. 4 is a plot of force, or load (lb$_f$) versus extension (inches) for a sample from an exemplary embodiment of lead coil 210 that has a one-inch (25 millimeters) gauge length. The plot was generated by an Instron test system with a 10 lb$_f$ (44.5 N/m) load cell that elongated the sample at a pull rate of 3 inches/minute (76 millimeters/min), and the data point at 4 inches (102 millimeters) extension (400% strain or a total of 5 inches (127 millimeters) in length) is indicated at a force/load of less than 0.1 lb$_f$ (0.4 N). (Other data points are recorded at 75%, 120% and 150% strain.) The one-inch (25 millimeters) gauge length of the sample is un-deformed, or un-stretched coil extending between clamped stretched out ends, wherein the Instron clamps are spaced at least one inch from the one-inch length of un-stretched coil.

According to the exemplary embodiment, single conductor coil 210 of lead 200 is close wound from a single cable conductor 32, for example, as depicted in the cross-section of FIG. 5. FIG. 5 illustrates cable conductor 32 including a plurality of conductive filaments 320 (for example, 0.0012 inch 20 micrometers) diameter medical grade 316L stainless steel wire) overlaid by an insulative layer 302 (for example, Ethylene Tetrafluoroethylene copolymer having a nominal thickness of 0.001 inch (25 micrometers)).

FIG. 5 further illustrates conductive filaments 320 of cable 32 arranged in a 1×19 configuration, concentric lay, which is known in the art, wherein the arrows in FIG. 5 indicate the left hand lay of seven inner filaments and the right hand lay of twelve outer filaments of filaments 320.

To provide uninsulated distal segment 21 UN of coil distal portion 210D, as well as the uninsulated section of coil proximal portion 210P that overlaps connector pin 260, insulative layer 302 is removed from around conductive filaments 320 by any suitable process known in the art. With further reference to FIGS. 2B-C, coil distal portion 210D defines an innermost surface of lead 200 that surrounds an elongate lumen 201 of lead 200, wherein an elongate bore of connector pin 260 defines a proximal-most portion of lead lumen 201 and a proximal opening thereof at pin proximal end 26 (FIG. 2A).

Furthermore, according to the illustrated embodiment, insulative layer 302 of cable 32 serves as a primary insulation for lead 200 and defines both the innermost surface of lead 200 and an outermost surface of lead 200 along insulated segment 211N of coil distal portion 210D. Thus, as indicated above, no turns of coil distal portion 210D are mechanically coupled together so that coil distal portion 210D can freely stretch and absorb the strain, as described above, without translating a force that can dislodge uninsulated distal segment 21UN. Lumen 201 may be sized to receive a stylet 400, which is described in greater detail below, in conjunction with FIGS. 7A-C.

According to some preferred embodiments, single cable conductor 32 is close wound to form lead 200 with a maximum diameter larger than that of a typical temporary medical electrical lead for sacral nerve stimulation, for example, being between 0.032 inch (813 micrometers) and 0.041 inch (1040 micrometers) along insulated segment 211N of coil distal portion 210D. This larger diameter of lead 200, in conjunction with material selection and the close-wound pitch of coil conductor 210, contributes to the relatively low force translated along coil distal portion 210D (lower than that of a typical temporary lead) when strained up to 400%, as described above.

In addition to providing strain relief that prevents uninsulated segment/electrode 21UN from dislodging from the sacral nerve stimulation site, the configuration of lead 200 facilitates removal thereof from the patient's body when the trialing period is complete by allowing an operator who explants lead 200 to stretch coil 210 to a smaller diameter with relative ease. Furthermore, as indicated above, the lack of a fixation component in the construction of lead 200 also allows for an easier removal of lead 200.

Figure 6A:
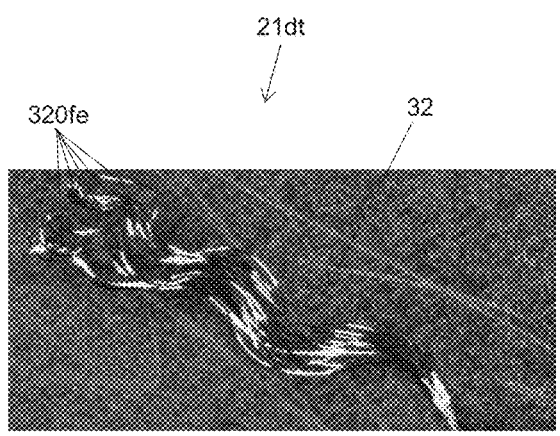
FIG. 6A is a photograph of an illustrative temporary medical electrical lead distal-most end that is free of mechanical coupling.

To further facilitate removal, and with reference to FIG. 6A, distal-most ends 320fe of conductive filaments 320 of cable 32, located at distal-most tip 21dt of lead 200 (FIG. 2A), are free of any mechanical coupling that could cause distal-most tip 21dt of lead 200 to enlarge by a 'bunching up' of cable filaments 320, due to differing filament lengths of the above-described 1×19 configuration of cable 32, as coil 210 is stretched during explant.

Figure 6B:
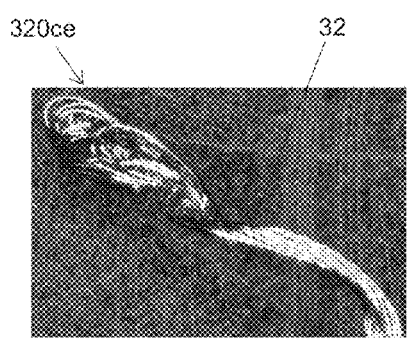
FIG. 6B is a photograph of a cable filament distal-most end that are mechanically coupled together by a laser weld.

FIG. 6B illustrates cable filament distal-most ends 320ce that are mechanically coupled together by a laser weld, according to the typical practice known in the art, when a coil formed from the 1×19 cable is stretched. Such a 'bunching up' has been found to increase the difficulty of explant by catching on tissue as the cable is pulled along the explant path.

Figure 7A:
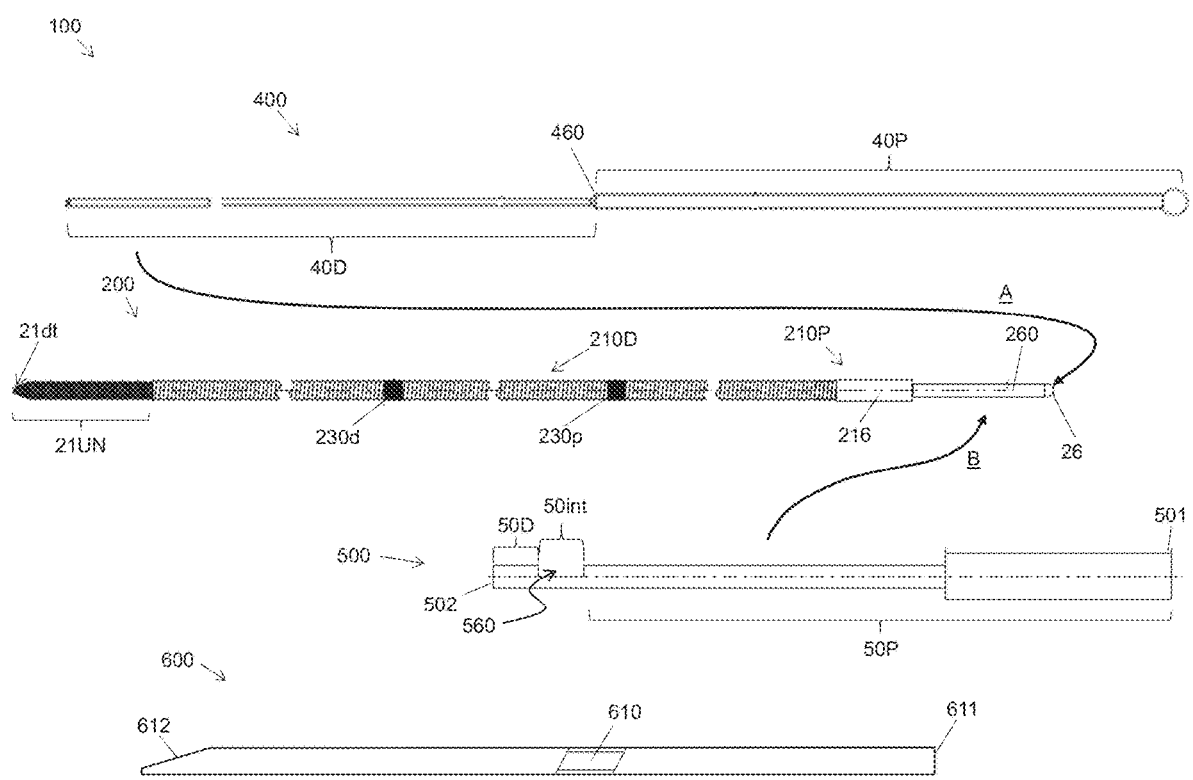
FIG. 7A is a schematic plan view of a system for providing temporary medical electrical stimulation utilizing the illustrative temporary medical electrical lead shown in FIG. 2A.
Figure 8:
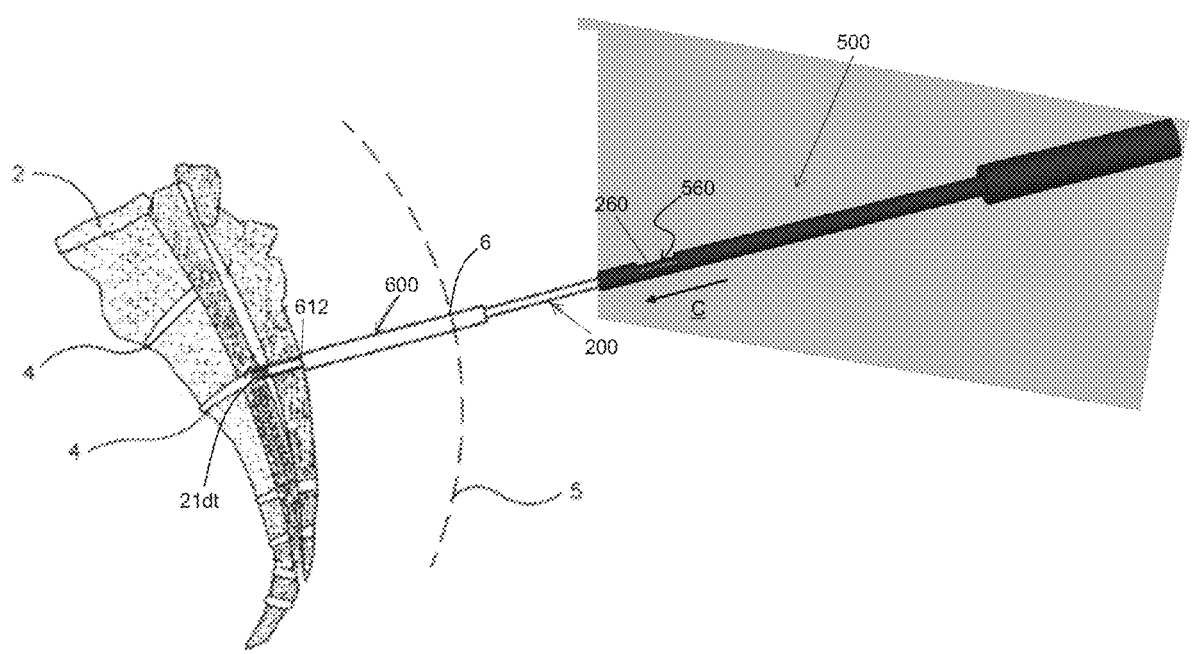
FIG. 8 is a schematic diagram showing an introducer needle positioned in the patient's body, with lumen distal opening located in proximity to one of the sacral foramina.

FIG. 7A is a plan view of a system 100 for providing temporary medical electrical stimulation, which includes the above-described lead 200. FIG. 7A illustrates system 100 including an introducer needle 600, the aforementioned stylet 400, and a grip tool 500 for temporarily securing stylet 400 to lead 200, for example, when an operator inserts lead 200 through introducer needle 600 for implant, for example, as illustrated in the schematic of FIG. 8.

According to the illustrated embodiment, introducer needle 600 has a lumen 610 sized to receive passage of the entire length of the temporary medical electrical lead 200 (for example, about 305 millimeters (12 inches)) therethrough, from a proximal opening 611 of needle lumen 610 to a distal opening 612 of needle lumen 610; and, according to an exemplary embodiment, introducer needle is a 18.5 gauge needle that may have a length of about 89 micrometers (3.5 inches) or a length of about 127 micrometers (5 inches).

FIG. 7A further illustrates lead 200 including markers 230d, 230p positioned along coil distal portion 210D to provide the operator with visual indicators of locations of lead distal-most tip 21dt, relative to needle lumen distal opening 612, as the operator advances lead 200 through needle lumen 610 for implant. According to an exemplary embodiment, a length of each marker 230d, 230p is about 0.1 inch (25 millimeters), marker 230d is spaced about 4.3 inches (109 millimeters) from distal-most tip 21dt (for example, for use with the aforementioned 3.5 inch (89 millimeters) long needle), and marker 230p is spaced about 5.8 inches (147 millimeters) from distal-most tip 21dt (for example, for use with the aforementioned 5 inch (127 millimeters) long needle). To allow coil distal portion 210D to freely stretch, as described above, markers 230d, 230p are constructed in a manner so that they do not mechanically couple turns of coil distal portion together, for example, by laser marking insulative layer of 302 of cable conductor 32. When insulative layer 302 is formed from Ethylene Tetrafluoroethylene copolymer that is loaded with a Titanium dioxide pigment, the laser marking darkens the white appearance of the loaded copolymer.

With further reference to FIG. 7A, stylet 400 includes a proximal length 40P and a distal length 40D. Distal length 40D has an outer diameter sized to fit in sliding engagement within elongate lumen 201 of lead 200 (FIG. 7B), and proximal length 40P has an outer diameter sized to abut proximal end 26 of lead connector pin 260, when distal length 40D is fitted within lead lumen 201, for example, at a shoulder 460 of stylet 400, which is a transition between proximal length 40P and distal length 40D.

Figure 7B:
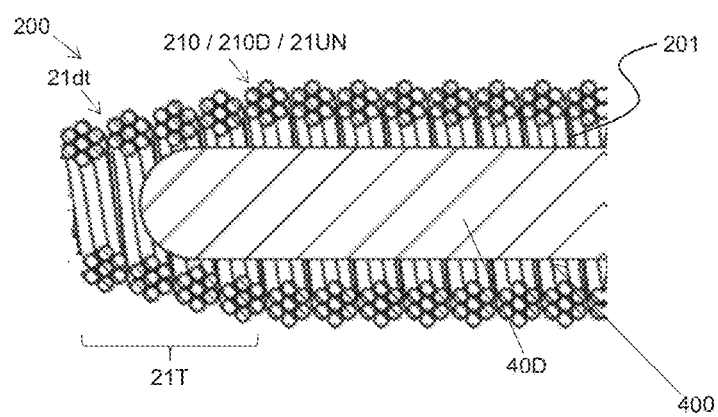
FIG. 7B is a schematic longitudinal section view of the illustrative temporary medical electrical lead at the distal-most tip.

FIG. 7B is a longitudinal section view of a portion of lead 200 at distal-most tip 21dt thereof, which shows stylet distal length 40D, having been inserted into lead lumen 201 at the proximal opening thereof (connector pin proximal end 26) per arrow A of FIG. 7A. According to some methods and embodiments, as an initial step in assembling system 100, stylet 400 is inserted into lead lumen 201 until stylet distal length 40D abuts lead distal-most tip 21dt, as shown, being stopped by the aforementioned tapered segment 21T of lead coil 210. Tapered segment 21T decreases in diameter, for example, over a length of no more than about 0.04 inch (102 millimeter), to an inner diameter that prevents stylet distal length 40D from protruding out from distal-most tip 21dt of lead 200.

Arrow B in FIG. 7A indicates a next step in assembling system 100, according to some methods, that involves securing lead 200 to the inserted stylet 400 by fitting a distal portion 50D of grip tool 500 around lead connector pin 260 and a proximal portion 50P of grip tool 500 around proximal length 40P of the inserted stylet 400. The above-described relatively low force translated along coil distal portion 210D of lead 200 when strained up to 400%, due in part to the larger than typical diameter thereof, makes lead 200 significantly limp relative to a stiffness of a of stylet distal length 40D that has a larger than typical diameter corresponding to the larger diameter of lead coil 210. Thus, if grip tool 500 were not employed to secure lead 200 to the inserted stylet 400, the operator may encounter difficulty in keeping lead 200 from sliding off of stylet 400 when inserting distal-most tip 21dt of lead 200 into stylet lumen 610 for implant.

Figure 7C:
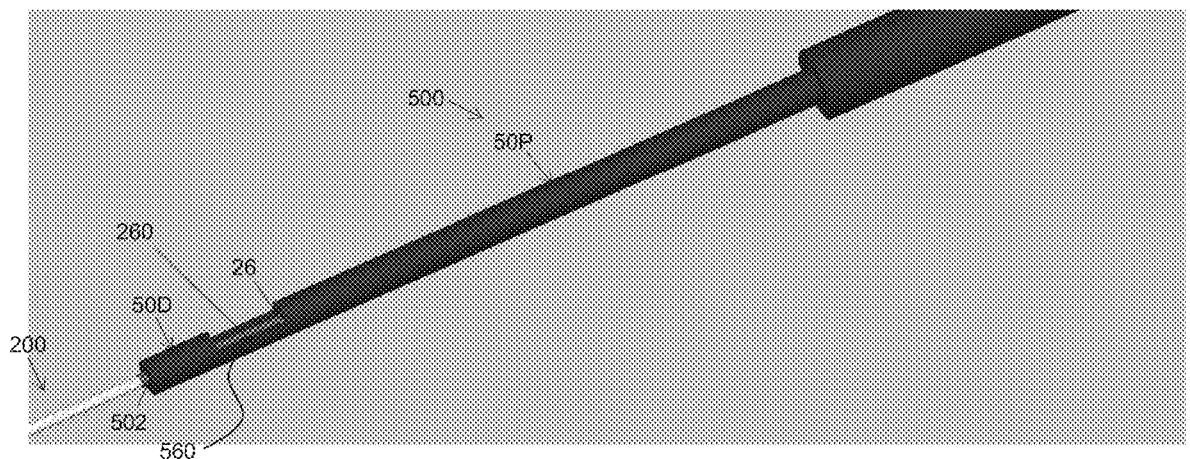
FIG. 7C is a schematic perspective view of an illustrative grip tool holding the illustrative temporary medical electrical lead.

The portions of grip tool 500 are preferably fitted around lead 200 and the inserted stylet 400 so that connector pin proximal end 26 abuts stylet proximal length 40P. Furthermore, grip tool 500 is shown having a window 560 formed along an intermediate portion 50int thereof (between distal portion 50D and proximal portion 50P), so that, when grip tool 500 is fitted, grip tool intermediate portion 50int can be located in proximity to the abutment of connector pin proximal end 26 with stylet proximal length 40P, thereby exposing lead connector pin 260 through window 560, as shown in FIG. 7C.

Figure 7D:
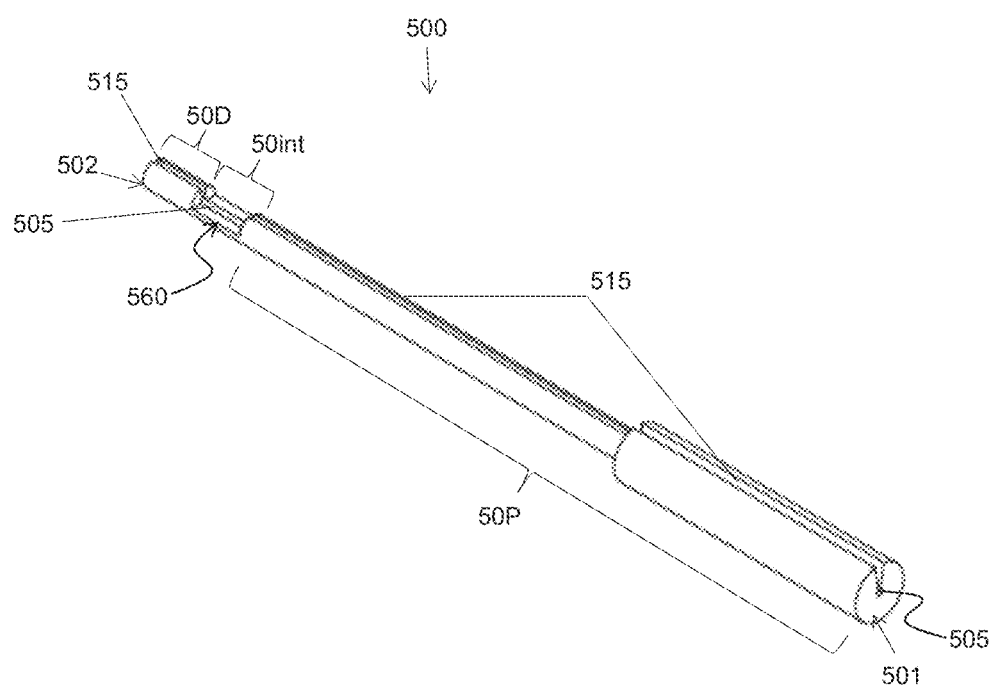
FIG. 7D is a schematic perspective view of the illustrative grip tool 500.

FIG. 7D is a perspective view of grip tool 500, according to some embodiments, wherein a means for the fitting of grip tool 500, as described above, is shown. FIG. 7D illustrates grip tool 500 including an elongate channel 505 extending along an entire length of tool 500, from a proximal end 501 thereof to a distal end 502 thereof, wherein channel 505 is sized to receive, in gripping engagement, lead 200 and stylet 400. FIG. 7D further illustrates grip tool 500 including an elongate slot 515 extending along channel 505 to provide access thereto for insertion and withdrawal of stylet 400 and lead 200. According to an exemplary embodiment, grip tool 500 may be formed, for example, from a medical grade silicone rubber by any suitable molding process known in the art.

FIG. 8 is a schematic showing introducer needle 600 positioned in the patient's body, with lumen distal opening 612 located in proximity to one of the sacral foramina 4. FIG. 8 further illustrates lead 200, with inserted stylet 400 secured thereto by grip tool 500, having been advanced through needle 600 until distal-most tip 21dt of lead 200 exits needle lumen distal opening 612.

According to some methods, the operator grips grip tool 500 to advance lead 200 through needle 600 and through foramen 4 until lead distal-most tip 21dt is located in proximity to the sacral nerves. The aforementioned close-wound construction of lead coil 210 makes distal-most tip 21dt responsive to the operator's push force applied in proximity to lead connector pin 260, and assures that the above-described markers 230d, 230p provide an accurate indication of the location of tip 21dt relative to needle lumen distal opening 612. Then, to determine if uninsulated distal segment/electrode 21UN of lead 200 is positioned properly to stimulate the sacral nerves, the operator may connect an external pulse generator to lead connector pin 260 through window 560 of grip tool 500, or may remove grip tool 500 prior to making the connection.

In either case, after determining that lead 200 is properly positioned and with grip tool 500 removed, to remove introducer needle 600 from around lead 200, the operator can retract introducer needle 600 while applying a push force to lead 200 with the inserted stylet 400, which push force is transferred to lead 200 by the aforementioned abutment of stylet proximal length 40P with lead connector pin proximal end 26. Thus, it may be appreciated that a diameter of stylet proximal length 40P is such to fit in sliding engagement within needle lumen 610 so that needle 600 can be retracted over stylet 400 as well as over the implanted lead 200. Furthermore, the above-described close-wound construction of lead coil 210 can provide tactile feedback to the operator that lead 200 is not advanced out of position by the push force applied to stylet 400 as the operator retracts needle 600.

In the foregoing detailed description, the invention has been described with reference to specific embodiments. However, it may be appreciated that various modifications and changes can be made without departing from the scope of the invention as set forth in the appended claims.

The invention claimed is:

1. A temporary medical electrical lead comprising:
a connector pin; and
a single conductor coil, the coil extending from a proximal portion to a distal portion and having a length, the coil being close-wound along the length thereof, the proximal portion of the coil coupled to the connector pin and a distal portion of the coil extending to a tapered distal-most tip of the lead, the distal portion of the coil defining an inner surface of the lead, the inner surface surrounding an elongate lumen of the lead, the connector pin including an elongate bore that defines a proximal-most portion of the elongate lumen and a proximal opening thereto at a proximal end of the connector pin;
no turns of the coil distal portion are mechanically coupled together; and
the coil distal portion translates a force of no greater than 0.1 lb$_f$ (0.4 N) when strained 400%.

2. The lead of claim 1, wherein:
the single conductor coil distal portion includes an insulated proximal segment and an uninsulated distal segment, the insulated segment extending from the coil proximal portion to the uninsulated segment, and the uninsulated segment extending from the insulated segment to the distal-most tip of the lead; and
the single conductor coil comprises a single cable, the cable comprising a plurality of conductive filaments and an insulative layer, the insulative layer extending around the conductive filaments along the insulated segment of the coil distal portion, but not along the uninsulated segment of the coil distal portion, and the insulative layer defining the inner surface and an outer surface of the lead along the insulated segment of the coil distal portion only.

3. The lead of claim 2, wherein the plurality of conductive filaments of the cable are arranged in a 1×19 configuration, concentric lay.

4. The lead of claim 2, wherein:
the plurality of conductive filaments of the cable are arranged in a 1×19 configuration, concentric lay, each filament having a diameter of about 0.0012 inch (30.5 micrometers); and
the insulative layer of the cable defines a maximum outer diameter of the lead along the coil distal portion, the maximum outer diameter being greater than 0.032 inch (813 micrometers) and less than 0.041 inch (1040 micrometers).

5. The lead of claim 3, further comprising a marker formed in the insulative layer of the cable, and wherein the insulative layer has a white appearance except for the marker.

6. The lead of claim 3, wherein each conductive filament of the cable has a distal-most end at the distal-most tip of the lead, the conductive filament distal-most ends being free of any mechanical coupling.

7. The lead of claim 1, wherein the coil distal portion translates a force of less than 0.1 lb$_f$ (0.4N) when strained 400%.

8. A system for providing temporary medical electrical stimulation, the system comprising the lead of claim 1, an introducer needle, a stylet, and a grip tool, and wherein:
the introducer needle has a lumen sized to receive passage of an entire length of the lead therethrough, from a proximal opening of the needle lumen to a distal opening of the needle lumen, the entire length of the lead being defined from the proximal end of the connector pin to the distal-most tip of the lead, the stylet includes a proximal length and a distal length, the distal length having an outer diameter sized to fit in sliding engagement within the elongate lumen of the lead, and the proximal length having an outer diameter sized to abut the proximal end of the connector pin of the lead, when the distal length is fitted within the lead lumen; and the grip tool being configured to engage with the lead and the stylet to temporarily secure the stylet to the lead when the distal length of the stylet is fitted within the elongate lumen of the lead, and when the proximal length of the stylet abuts the connector pin of the lead.

9. The system of claim 8, wherein the grip tool extends over a length from a proximal end thereof to a distal end thereof, and the grip tool further comprising:

a distal portion extending from the distal end of the tool;

a proximal portion extending between the distal portion of the tool and the proximal end of the tool;

an elongate channel extending along the length of the tool from the proximal end to the distal end thereof, the channel being sized to receive in gripping engagement the lead, within the distal portion of the tool, and the proximal length of the stylet within the proximal portion of the tool, when the distal length of the stylet is fitted within the elongate lumen of the lead and the proximal length of the stylet abuts the connector pin of the lead; and an elongate slot extending along the channel, the slot providing access to the channel for insertion and withdrawal of the lead into and out from the distal portion of the tool, and insertion and withdrawal of the proximal length of the stylet into and out from the proximal portion of the tool.

10. The system of claim 9, wherein the grip tool further comprises an intermediate portion extending between the distal and proximal portions thereof, the intermediate portion configured with a window to expose the lead connector pin when the tool temporarily secures the stylet to the lead.

11. A method for assembling a system, the system comprising the lead of claim 1 and a stylet, the stylet being configured to fit in sliding engagement within the elongate lumen of the lead; and the method comprising:

inserting a distal length of the stylet into the elongate lumen of the lead from the proximal opening thereof, until the distal length of the stylet abuts the distal-most tip of the lead; and securing the lead to the inserted stylet, the securing comprising fitting a distal portion of a grip tool around the lead connector pin and a proximal portion of the grip tool around a proximal length of the inserted stylet, so that the proximal end of the connector pin abuts the proximal length of the inserted stylet.

12. The method of claim 11, wherein securing the lead to the inserted stylet further comprises locating an intermediate portion of the grip tool in proximity to the abutment of the lead connector pin proximal end with the stylet proximal length, the intermediate portion of the grip tool extending between the distal and proximal portions of the grip tool and being configured to expose the lead connector pin.

13. A method of implanting the lead included in the system according to claim 11, the method comprising:

passing the distal-most tip of the lead into a lumen of a positioned introducer needle through a proximal opening thereof, the needle being positioned in a patient's body with a distal opening of the needle lumen located in proximity to a sacral foramen;

advancing the lead through the needle lumen until the distal-most tip of the lead exits the distal opening of the needle lumen and passes through the foramen so that the distal-most tip is located in proximity to a sacral nerve, the advancing comprising gripping the tool that secures the lead to the inserted stylet;

removing the grip tool from around the advanced lead and inserted stylet; and removing the introducer needle from around the advanced lead, after removing the grip tool, the removing of the needle comprising applying a push force to the lead with the inserted stylet while retracting the needle from the patient's body, the push force being transferred through the abutment of the proximal length of the stylet with the proximal end of the lead connector pin.

14. A method of implanting the lead included in the system according to claim 8, the method comprising:

passing the distal-most tip of the lead into the lumen of the introducer needle through the proximal opening thereof, the lead having had the distal length of the stylet inserted into the lead lumen, and the needle having been positioned in a patient's body with the distal opening of the needle lumen located in proximity to a sacral nerve;

advancing the lead through the needle lumen until the distal-most tip of the lead exits the distal opening of the needle lumen, the advancing comprising gripping the grip tool, the grip tool having been engaged with the lead and the inserted stylet to secure the lead to the inserted stylet so that the proximal length of the stylet abuts the proximal end of the lead connector pin;

removing the grip tool from around the advanced lead and inserted stylet; and removing the introducer needle from around the advanced lead, after removing the grip tool, the removing of the needle comprising applying a push force to the lead with the inserted stylet while retracting the needle from the patient's body, the push force being transferred through the abutment of the proximal length of the stylet with the proximal end of the lead connector pin.

15. The method of claim 14, further comprising engaging the grip tool with the lead and the inserted stylet so that a window of the grip tool is located in proximity to the abutment of the proximal length of the stylet and the proximal end of the lead connector pin, and so that the window exposes the lead connector pin.

16. A temporary medical electrical lead comprising:

a connector pin; and a single conductor coil formed of a beta-titanium alloy, the coil extending from a proximal portion to a distal portion and having a length, the coil being close-wound along the length thereof, the proximal portion of the coil coupled to the connector pin and a distal portion of the coil extending to a tapered distal-most tip of the lead, the distal portion of the coil defining an inner surface of the lead, the inner surface surrounding an elongate lumen of the lead, the connector pin including an elongate bore that defines a proximal-most portion of the elongate lumen and a proximal opening thereto at a proximal end of the connector pin;

no turns of the coil distal portion are mechanically coupled together; and the coil distal portion translates a force of no greater than 0.1 $lb_f$ (0.4 N) when strained 400%.

17. The lead of claim 16 wherein, the beta-titanium alloy is Ti-15Mo.

\* \* \* \* \*